United States Patent [19] … [11] Patent Number: 4,931,040
Haber et al. … [45] Date of Patent: Jun. 5, 1990

[54] SAFETY SYRINGE HAVING A COMBINATION NEEDLE CANNULA AND ARTICULATING HUB FOR RETRACTING SAID CANNULA INTO A MEDICATION CARPULE

[75] Inventors: Terry M. Haber, Lake Forest; Clark B. Foster, El Toro, both of Calif.

[73] Assignee: Habley Medical Technology, Laguna Hills, Calif.

[21] Appl. No.: 181,204

[22] Filed: Apr. 13, 1988

[51] Int. Cl.⁵ ............................................. A61M 5/00
[52] U.S. Cl. ................................ 604/110; 604/195; 604/232
[58] Field of Search ........ 604/110, 192, 195, 196–198, 604/228–229, 232, 234, 235

[56] References Cited

U.S. PATENT DOCUMENTS

| | | | |
|---|---|---|---|
| 2,671,450 | 3/1954 | Dann | 604/192 |
| 3,848,593 | 11/1974 | Baldwin | 604/232 |
| 4,333,457 | 6/1982 | Margulies | 604/110 |
| 4,493,703 | 1/1985 | Butterfield | 604/118 |
| 4,507,117 | 3/1985 | Vining et al. | 604/228 |
| 4,675,005 | 6/1987 | Deluccia | 604/110 |
| 4,747,830 | 5/1988 | Gloyer et al. | 604/110 |
| 4,747,831 | 5/1988 | Kulli | 604/110 |
| 4,790,822 | 12/1988 | Haining | 604/110 |

Primary Examiner—C. Fred Rosenbaum
Assistant Examiner—Michael Rafa
Attorney, Agent, or Firm—Morland C. Fischer

[57] ABSTRACT

A safety syringe, such as a dental syringe, comprising a hollow cylinder, a disposable, prefilled fluid medication carpule received within the interior of the cylinder, and a needle carrying hub supporting a needle cannula so that the cannula extends axially from the carpule and outwardly of the cylinder, whereby to administer an injection. A piston assembly is movable axially through the carpule to first expulse the medication therefrom and to then engage and retract the needle hub and its associated needle cannula into the carpule, so that the needle will be completely surrounded and shielded by said carpule. A slide lock is connected around one end of the medication carpule and interfaced with the needle carrying hub to control the relocation of the hub and corresponding retraction of the cannula through the carpule. The slide lock is selectively moved relative to the carpule between needle retaining and needle releasing positions to either anchor the needle carrying hub with the needle extending axially from the carpule for administering an injection or release the needle carrying hub for retracting the cannula into its carpule to permit a safe disposal of the needle while avoiding an accidental and potentially life threatening needle strike.

22 Claims, 3 Drawing Sheets

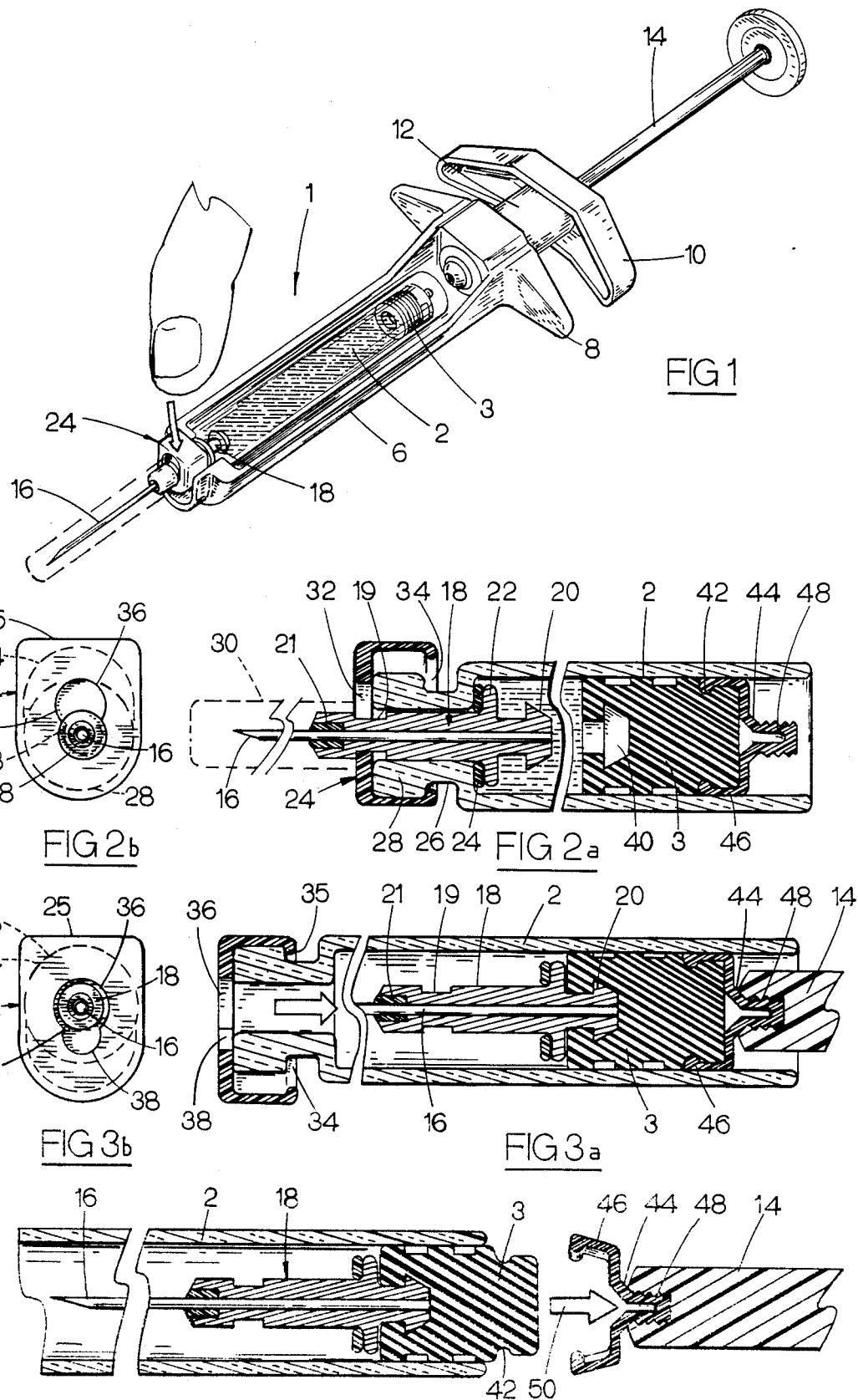

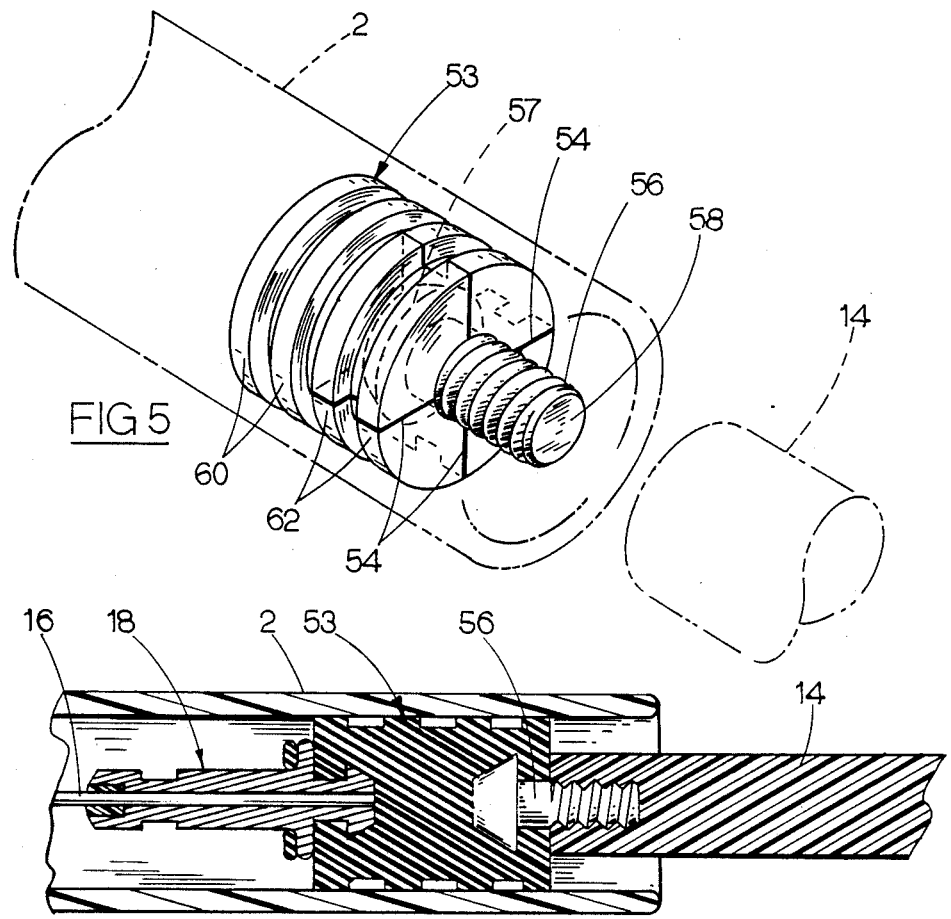
FIG 5
FIG 6
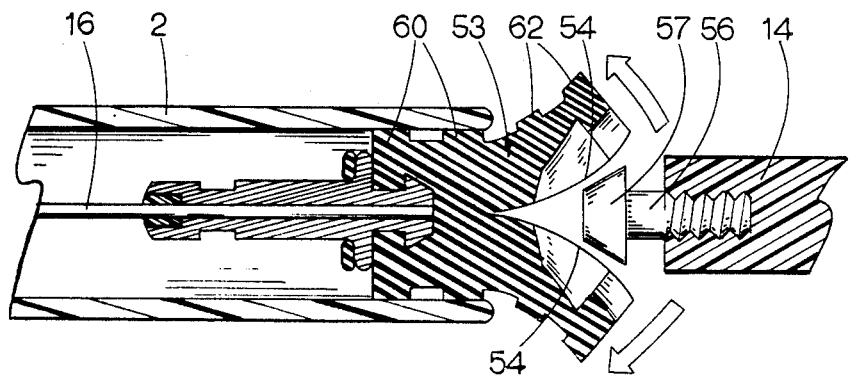
FIG 7

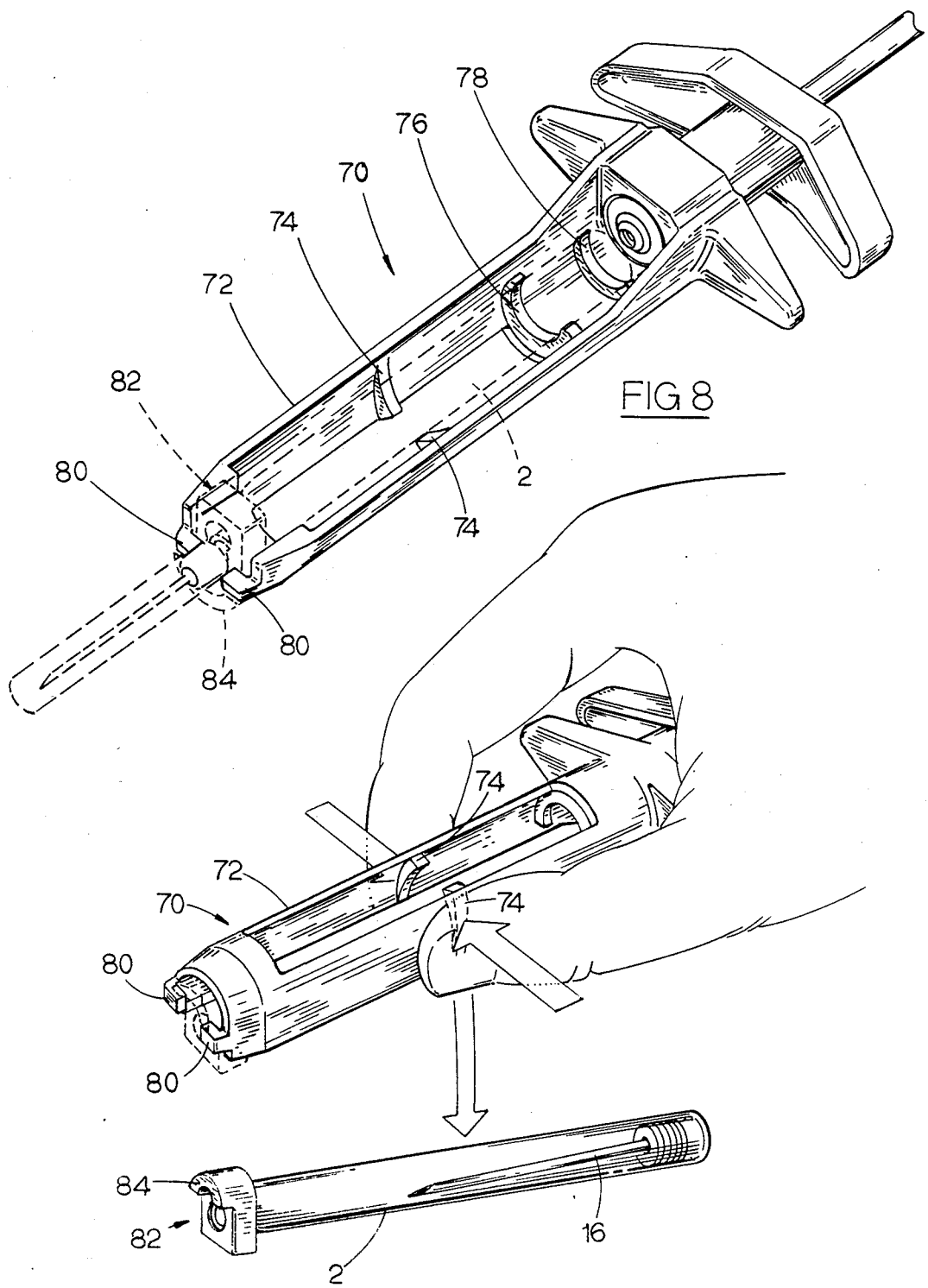

# SAFETY SYRINGE HAVING A COMBINATION NEEDLE CANNULA AND ARTICULATING HUB FOR RETRACTING SAID CANNULA INTO A MEDICATION CARPULE

BACKGROUND OF THE INVENTION

1. Field of the Invention

This invention relates to a safety syringe having a disposable, prefilled medication carpule and a combination needle retaining hub and needle cannula, and to a slide lock which is connected to the carpule and movable from a needle retaining position, at which the cannula is anchored so as to project axially from the carpule for administering an injection, to a needle releasing position, at which the cannula may be retracted within and completely shielded by the carpule.

2. Prior Art

Syringes of the type having a prefilled carpule of fluid medication and a hypodermic needle cannula are well known in the art for injecting such medication from the carpule to a targeted tissue area of a patient. However, at the completion of the injection, the needle is typically locked in an axially extended position projecting outwardly from the syringe cylinder. In some cases, the syringe may be used to treat a patient having a communicable disease. Prior to disposing the syringe, the hypodermic needle is frequently broken or destroyed to prevent reuse. Medical workers are especially susceptible to accidental and potentially infectious needle strikes due to the careless handling or breaking of the needle cannula and disposing of the syringe after use. The resulting mini-accident caused by an accidental needle strike typically requires a blood test for such diseases as AIDS and hepatitis. The corresponding cost and inefficiency of testing medical workers who have received such an accidental needle strike result in considerable waste, which may be particularly damaging to a medical facility which is striving for economy.

The following patent application, which has been or will be assigned to the assignee of the present patent application, discloses a syringe including a prefilled medication carpule and means for retracting a needle cannula into said carpule after an injection has been administered: application Ser. No. 143,751 filed January 14, 1988 by Terry M. Haber et al.

SUMMARY OF THE INVENTION

In general terms, a safety syringe is disclosed which comprises a hollow syringe cylinder in which to receive a disposable, prefilled medication carpule. A combination needle carrying hub and needle cannula are movable axially through the carpule. Initially, the hub is retained at a distal end of the carpule so that the cannula extends axially from the carpule and outwardly of the cylinder for administering an injection. A piston is initially located at the proximal end of the carpule and movable axially through the carpule for expulsing the medication therefrom. The piston includes a receptacle for engaging and retaining the needle hub.

A slide lock is connected around the distal end of the carpule to be interfaced with the needle hub. The slide lock includes a pair of overlapping holes formed in a front face thereof. One of the holes has a diameter which is larger than the diameter of the second hole. The slide lock is adapted to be moved laterally relative to the medication carpule from a needle retaining position, at which the needle hub is received through the hole of relatively small diameter, to a needle releasing position, at which the needle hub is received through the hole of larger diameter.

In operation, the slide lock is initially located in the needle retaining position, whereby relocation of the needle hub is blocked by the small diameter hole. Thus, the needle cannula extends axially from the carpule for administering an injection. A piston stem is detachably connected to the piston for driving the piston axially and distally through the carpule and expulsing the contents thereof. The piston is attached at the receptacle thereof to the needle hub when the piston is driven to the distal end of the carpule. After the injection has been administered, the slide lock is moved to the needle releasing position, whereby relocation of the needle hub is available through the large diameter hole. The piston stem is withdrawn axially and proximally through the carpule, whereby to correspondingly retract the needle hub and its associated cannula into the carpule. The piston stem is then detached from the piston and discarded. The carpule can be removed from the syringe cylinder with the needle cannula completely surrounded and shielded therewithin. Accordingly, the carpule may be safety discarded without having to handle or destroy the cannula so as to advantageously eliminate the risk of an accidental and potentially life threatening needle strike.

BRIEF DESCRIPTION OF THE DRAWINGS

FIG. 1 is an isometric view of a safety syringe having a combination needle hub and needle cannula which may be retracted into the interior of a disposable medication carpule;

FIG. 2a is a cross section of the syringe of FIG. 1 with the combination needle hub and cannula extending axially from the carpule;

FIG. 2b is a front view of the syringe of FIG. 1;

FIG. 3a is a cross section of the syringe of FIG. 1 with the combination needle hub and cannula retracted within the carpule;

FIG. 3b is a front view of the syringe of FIG. 3a;

FIG. 4 shows one embodiment for detaching a piston stem from a piston of the carpule;

FIGS. 5–7 show an alternate embodiment for detaching a piston stem from a piston; and FIGS. 8 and 9 show another safety syringe and means for ejecting the medication carpule from the syringe cylinder with the cannula surrounded and shielded by the carpule.

DESCRIPTION OF THE PREFERRED EMBODIMENTS

Details of the combination needle cannula and articulating needle hub which form the present invention are now described while referring to the drawings. The aforementioned combination is particularly useful to syringes having a prefilled medication carpule from which a fluid medication is injected into a targeted tissue area of a patient. By way of example, a syringe which typically uses a prefilled medication carpule is a dental syringe. To this end, FIG. 1 of drawings shows a safety syringe 1 having a disposable medication carpule 2 into which a hypodermic needle cannula 16 may be retracted and discarded. Carpule 2 is typically formed from a transparent material such as plastic or glass. A piston 3 is located in and movable axially through the carpule 2. The carpule 2 is carried in and manipulated by a reusable, combination cylinder, retaining collar, and piston stem. One such combination is sold commercially under the name CARPUJECT by Winthrop-Breon Corporation of New York. However, it is to be understood that the aforementioned combination, in and of itself, forms no part of the present invention. Therefore, for purposes of clarity, only a brief description is now provided of said combination.

The combination syringe cylinder, retaining collar, and piston stem for syringe 1 includes a hollow, elongated cylinder 6 having open proximal and distal ends. The medication carpule 2 is removably received at the hollow interior of cylinder 6. The front face of the cylinder 6 is removed so that a health care worker will have visible access to the entire carpule 2 being carried therewithin. The proximal end of cylinder 6 terminates at an integral, radially projecting flange 8 under which the fingers of a health care worker are placed during the administration of an injection. Located above and extending in parallel alignment with the flange 8 is a radially projecting locking handle 10 having a longitudinally extending hollow retaining collar 12. The hollow retaining collar 12 of locking handle 10 has a cammed surface (not shown) which is received through an opening in flange 8. An elongated piston stem 14 extends through a hole in locking handle 10 and the hollow interior of retaining collar 12 to be detachably connected to the piston 3 of carpule 2 for controlling the axial movement of piston 3 through carpule 2 in a manner that will be described in greater detail hereinafter when referring to FIGS. 2 and 3. To complete the assembled combination, the locking handle 10 is rotated through a 180 degree arc around piston stem 14, whereby the cammed retaining collar 12 is advanced through the open proximal end of cylinder 6 and into contact with the proximal end of carpule 2. Accordingly, the retaining collar 12 of locking handle 10 will surround and releasably retain the carpule 2 at the interior of syringe cylinder 6 so that an injection may be administered.

The syringe 1 is provided with a hypodermic needle cannula 16 which communicates with the carpule 2 so that the fluid contents of carpule 2 may be expulsed therefrom via cannula 16. The needle cannula 16 is supported at and carried by a needle hub 18 which is preferably formed from an inert (e.g. ceramic or glass) material so as to avoid a reaction between hub 18 and the medication of carpule 2.

Referring concurrently to FIGS. 1-3 of the drawings, the hub 18 is shown with a longitudinally extending channel in which to receive needle cannula 16. The cannula 16 is preferably bonded to hub 18 by means of an appropriate (e.g. epoxy) joint 21 as is best shown in FIGS. 2a and 3a. A peripheral groove 19 is formed around one end of needle hub 18. A plug 20 is integrally formed with hub 18 at the opposite end in which groove 19 is formed. A disk-like flange 22 is formed around the periphery of hub 18 intermediate the groove 19 and end plug 20. A rubber seal or gasket 24 is seated below the flange 22. Seal 24 engages the distal end wall of carpule 2 to prevent the escape of fluid therepast when the retractable needle cannula 16 and hub 18 are located at the distal end of the carpule (best shown in FIG. 3a) prior to the administration of an injection.

In accordance with the present invention, the syringe 1 is provided with a slide lock 24, whereby the needle cannula 16 and its hub 18 can either be securely locked at a relatively distal position relative to carpule 2, at which the contents of carpule 2 may be injected via cannula 16 (illustrated in FIG. 2a), or released from said distal position and retracted to a relatively proximal position within carpule 2 after the contents of said carpule have been expulsed so that the cannula is completely surrounded and shielded by the carpule 2 (illustrated in FIG. 3a). In this manner, the carpule 2 may be disposed of after use with the needle cannula 16 safely and irretrievably located therein so as to avoid both the necessity of handling the needle and the possibility of an accidental and potentially life threatening needle strike.

More particularly, and referring to FIGS. 2 and 3 of the drawings, the slide lock 24 is adapted to be received in the narrow neck 26 and around the distal head 28 of carpule 2 which are standard to conventional disposable medication carpules. Hence, the slide lock 24 is advantageously applicable to virtually all medication carpules without requiring any modification thereto. Moreover, the carpule may be packaged with needle cannula 16, needle hub 18, and slide lock 24 assembled in place, so that health care workers may take advantage of the present invention by merely inserting the complete carpule assembly into the cylinder of an appropriate safety syringe. Of course, such a carpule assembly is packaged with a well known removable needle sheath 30 surrounding and protecting cannula 16.

Slide lock 24 is preferably formed from a resilient plastic material and is provided with a hollow, body having a flat finger pad 25 formed at one end thereof. The hollow, interior of slide lock 24 is generally elliptical in shape and characterized by a length along its major axis which is longer than the outside diameter of the head 28 of carpule 2. The elliptical interior of slide lock 24 is also characterized by a width along its minor axis which is approximately equal to the outside diameter of head 28. Opposing front and rear faces of slide lock 24 have respective openings 32 and 34 formed therethrough. Front opening 32 has a keyhole configuration (best shown in FIGS. 2b and 3b), the purpose of which will soon be described. Rear opening 34 is surrounded by an elliptical, peripheral lip 35. The rear opening 34 is characterized by a length which is longer than the outside diameter of the head 28 of carpule 2 and a width which is slightly narrower than the outside diameter of head 28.

In the assembled relationship of FIGS. 2 and 3, the head 28 of carpule 2 is gently forced through the rear opening 34 of resilient slide lock 24 and into the hollow interior thereof, whereby the peripheral lip of slide lock 24 is snapped around the narrow neck 26 of the incoming carpule 2. Thus, slide lock 24 cannot inadvertently detach from the carpule 2, because the width of the rear opening 34 is slightly less than the diameter of the head portion 28 and the peripheral lip which defines rear opening 34 is snapped into engagement with the carpule 2 at the narrow neck 26 thereof. Inasmuch as the length of the hollow interior of slide lock 24 is longer than the diameter of head portion 28, the slide lock 24 is free to slide laterally along head portion 28 between a needle locking position (of FIGS. 2a and 2b) and a needle releasing position (of FIGS. 3a and 3b).

As previously disclosed, the front opening 32 of slide lock 24 has a key hole configuration. More particularly, and is best shown in FIGS. 2b and 3b, front opening 32 includes a pair of overlapping circular holes 36 and 38. That is to say, holes 36 and 38 lie on a common axis. However, the diameter of hole 36 is larger than the diameter of hole 38. The diameter of hole 36 is also larger than the maximum diameter of needle carrying hub 18. The diameter of hole 38 is less than the maximum diameter of needle carrying hub 18. The advantage of making front opening 32 with overlapping holes 36 and 38 of different diameters will soon be described.

As was previously disclosed when referring to FIG. 1, the carpule 2 includes a piston 3 which is movable axially through the carpule by means of a detachable piston stem 14. The details of piston 3 and its detachable connection to piston stem 14 are now described while continuing to refer to FIGS. 2a and 3a of drawings. Piston 3 is preferably formed from a resilient (e.g. rubber) material. At one end of piston 3, there is formed a hollow receptacle 40. Receptacle 40 has a configuration which is adapted to receive therewithin and retain the proximally projecting end plug 20 of needle hub 18. An annualar groove 42 is formed around the periphery of piston 3 at the opposite end thereof in which receptacle 40 is formed. Piston stem 14 is connected to piston 3 via a removable insert 44. Insert 44 has one or more pairs of jaws 46 which are formed from a resilient material and possess a spring-like memory. The jaws 46 of insert 44 have respective inwardly projecting teeth which are adapted to be releasably received within the annualar groove 42 of piston 3. That is, the cylindrical walls of the medication carpule 2 will hold the jaws 46 in a state of compression, such that the teeth of jaws 46 are rotated into communication with the piston 3 at the annualar groove 42 thereof. Insert 44 also has a screw threaded rod 48 extending therefrom. A complementary screw threaded receptacle is formed in the piston stem 14, whereby rod 14 can be rotated into engagement with piston 3 with the screw threaded rod 48 of insert 44 being mated to the screw threaded receptacle of said piston stem.

The operation of the syringe 1 in which the combination needle cannula 16 and articulating hub 18 are utilized is now described while referring concurrently to FIGS. 1–4 of drawings. Initially, the carpule 2 (with cannula 16, needle hub 18, and slide lock 24 interconnected therewith in the manner described above) is removed from its package and placed within the open faced cylinder 6 of syringe 1. In the pre-injection mode of FIG. 1, carpule 2 is filled with medication and the piston 3 is located at a proximal position therewithin. Needle hub 18 is disposed at the distal aspect of carpule 2, such that needle cannula 16 extends axially outward from the open distal end of syringe cylinder 6. The piston stem 14 is then rotated into engagement with the threaded rod 48 of insert 44 to form a piston assembly comprising piston 3 and stem 14. Next, the locking handle 10 is rotated 180 degrees around the piston stem 14 to advance the hollow retaining collar 12 of handle 10 axially through the proximal end of cylinder 6 and into receipt of the proximal end of carpule 2 so as to prevent the displacement of carpule 2 through the cylinder 6.

In the pre-injection mode of FIG. 1, the slide lock 24 is located in a needle locking position. More particularly, the slide lock 24 is initially located so that the needle hub 18 is received through the relatively small diameter hole 38 at the front face of slide lock 24. At the needle locking position, the peripheral groove 19 of needle hub 18 extends through and is engaged at the small diameter hole 38. That is to say, since the diameter of hole 38 is smaller than the maximum diameter of hub 18, the hub is blocked from being displaced proximally through said hole 38. Accordingly, the hub 18 is locked at the distal aspect of medication carpule 2 with needle cannula 16 projecting distally therefrom for administering an injection at a targeted tissue area.

To administer an injection during an injection mode (represented by FIGS. 2a and 2b), the health care worker applies an axial force to piston stem 14, whereby to drive the piston 3 distally through the carpule 2. The fluid contents of carpule 2 are expulsed therefrom via cannula 16. The piston 3 continues to be advanced distally through carpule 2 until all of the medication is expulsed from carpule 2, whereby receptacle 40 of piston 3 is moved into receipt of the end plug 20 of needle hub 18.

After the injection has been administered (and with the piston 3 attached to the hub 18 by means of the engagement of end plug 20 by receptacle 40), the slide lock 24 is moved to the needle releasing position. More particularly, the health care worker uses his finger to press upon the finger pad 25 of slide lock 24 and thereby cause the slide lock to move laterally relatively to the head 28 of carpule 2 from the needle retaining position to the needle releasing position. Accordingly, needle hub 18 now extends through the hole 36 of slide lock 24 which is of relatively large diameter.

The health care worker then applies an axial pulling force to piston stem 14, whereby to relocate piston 3 and withdraw the needle hub 18 proximally through the empty medication carpule 2. That is to say, inasmuch as the diameter of hole 36 is larger than the maximum diameter of needle hub 18, said hub is free to be relocated from the distal end of carpule 2. The proximal relocation of needle hub 18 causes a corresponding retraction of cannula 16 into medication carpule 2 so that the cannula is completely surrounded and shielded by the carpule. The healh care worker continues to apply an axial pulling force to piston stem 14 until insert 44 is removed from the proximal end of carpule 2. At this location, the spring-like memory of jaws 46 of insert 44 will rotate said jaws out of engagement with the groove 42 of piston 3. Hence, the piston stem 14 is automatically detached from piston 3 to be discarded. However, the needle cannula 16 remains irretrievably surrounded and shielded by the carpule 2. By virtue of the foregoing, the carpule 2 may be removed from syringe 1 and discarded with cannula 16 located safely within said carpule so as to avoid handling the cannula and the possibility of an accidental needle strike and the spread of a contagious and, possibly life threatening, disease.

FIGS. 5–7 show an alternate embodiment of the present invention. More particularly, the piston 3 of FIGS. 1–4 is modified with regard to the means of detaching the piston stem from the piston after the needle cannula 16 has been retracted proximally through the medication carpule 2 following the administration of an injection. As is best shown in FIG. 5, the modified piston 53 includes a series of radially extending slits 54 which are formed (e.g. cut) into the proximal end thereof. By way of example only, four radially extending slits 54 are shown spaced evenly around piston 53 at 90 degree angles of separation. A connector 56, formed from metal or the like, has a relatively large head 57 and a narrow screw threaded rod 58 formed at opposite ends, and is adapted to be detachably connected to piston 53 at the intersection of the slits 54. That is, the head 57 of connector 56 is received in a correspondingly shaped receptacle formed within the resilient body of piston 53.

The threaded rod 58 of connector 56 projects outwardly from piston 53 for engagement with the piston stem 14 in the same manner that the screw threaded rod 48 of insert 44 is engaged by the piston stem 14 in the embodiment of FIGS. 1-3.

Piston 53 is provided with a series of (e.g. four) peripheral ridges 60 and 62. At least some of the distally oriented ridges 60 of piston 53 have a diameter which is larger than the diameter of the remaining proximally oriented ridges 62. The advantage of having the distal end of piston 53 with a larger diameter than the proximal end thereof will be explained shortly.

In operation, and as best illustrated in FIG. 6, after the administration of an injection, the needle cannula 16 and its associated needle hub 18 are retracted proximally through carpule 2, as earlier described, by pulling piston stem 14 axially and proximally through said carpule. In FIG. 7, the piston 53 is relocated to the proximal end of carpule 2 such that the ridges 62 of relatively small diameter are removed from the carpule. However, the ridges 60 of piston 53 having a relatively large diameter maximize the frictional engagement of piston 53 by carpule 2 and thereby resist the removal of the piston from the carpule. As the health care worker continues to pull the piston stem 14 axially and proximally, a corresponding axial force is transferred from piston stem 14 to connector 56 to cause the connector head 57 to be pulled out of piston 53. More particularly, the pulling force applied to connector 56 coupled with the frictional force applied to piston 53 have the net effect of causing the segments of the resilient piston 53 which lay between slits 54 to be rotated outwardly, whereby to release connector head 57 from said piston. Accordingly, the connector 56 is detached from piston 53 to be discarded along with piston stem 14. However, the needle cannula 16 remains safely surrounded and shielded by the empty medication carpule 2 to avoid handling the cannula and thereby prevent an accidental and potentially life threatening needle strike.

FIGS. 8 and 9 of the drawings illustrate yet another embodiment of the present invention. More particularly, the cylinder of the safety syringe is modified to facilitate the removal and disposal of the medication carpule after an injection has been administered and the needle cannula has been retracted into and shielded by such carpule. As is best shown in FIG. 8, the cylinder 72 of modified safety syringe 70 is provided with a pair of integrally formed ejection arms 74. Cylinder 72 is also provided with a pair of axially spaced and arcuately shaped cradles 76 and 78. Cradle 76 is dimensioned so that a medication carpule 2 will be snapped into releasable receipt by cradle 76 when said carpule is loaded through the open front face of syringe cylinder 72. Cradle 78 is dimensioned to support the proximal end of the carpule 2 so that the carpule is retained in uniformly spaced, concentric alignment with cylinder 72. The ejection arms 74 face one another from opposite sides of cylinder 72. Ejection arms 74 are angled in a radially inward direction to facilitate the expulsion of carpule 2 from retaining cradle 76 and syringe cylinder 72 in a manner that will soon be disclosed.

The distal aspect of syringe cylinder 72 includes an integral pair of oppositely disposed support arms 80. Support arms 80 project radially inward in spaced, face-to-face alignment with one another. In the assembled configuration of FIG. 8, the support arms 80 engage the slide lock 82 to prevent the accidental removal of the combination slide lock 82 and medication carpule 2 from cylinder 72. To this end, the slide lock 82 includes a longitudinally extending and integrally formed end cap 84 (best shown in FIG. 9). The slide lock 82 is received within the open distal end of cylinder 72, such that the end cap 84 of slide lock 82 is located below and in contact with the opposing support arms 80, whereby the unintended displacement of slide lock 82 relative to cylinder 72 can be avoided. The slide lock 82 of FIGS. 8 and 9 includes the same number and orientation of front and rear openings that were previously described when referring to the slide lock 24 of FIGS. 1-4. Therefore, for purposes of brevity, the structure and operation of slide lock 82 will not again be described.

A description of the ejection capability of the safety syringe 70 is now described while referring to FIG. 9. After an injection has been administered and the needle cannula 16 retracted within the empty medication carpule 2, the health care worker grasps the syringe cylinder 72 between his thumb and index finger and applies equal and opposite radially inward directed forces to the cylinder above the opposing ejection arms 74. Accordingly, the sides of cylinder 72 are rotated towards one another. The rotational movement of cylinder 72 is transferred from the ejection arms 74 to the carpule 2, whereby to cause carpule 2 to pop out of the cradle 76 into which said carpule had been snapped. The continued application of the radially inward forces to cylinder 72 and the corresponding rotational movement of ejection arms 74 against carpule 2 will eject the carpule from the cylinder 72 through the open face thereof. Thus, the needle cannula 16 and its medication carpule may be safely, easily, and reliably discarded (such as into a conventional Sharp's container or the like) without requiring any handling by the health care worker.

It will be apparent that while a preferred embodiment of the invention has been shown and described, various modifications and changes may be made without departing from the true spirit and scope of the invention.

Having thus set forth a preferred embodiment of the invention, what is claimed is:

1. A syringe including a cylinder having proximal and distal ends, said cylinder receiving a supply of fluid, and a hypodermic needle cannula extending outwardly from the distal end of said cylinder and communicating with the fluid supply thereof so that fluid may be injected from said cylinder via said cannula, said syringe also including:

a carpule located at the interior of said cylinder and containing said supply of fluid, said needle cannula communicating fluidically with said carpule and the fluid therewithin, said carpule including a piston which is moved axially therethrough so that the fluid of said carpule is expulsed via said needle cannula in order to administer an injection;

a needle hub attached to said needle cannula and interfaced with said carpule at the distal end of said cylinder for retaining and supporting said cannula in fluid communication with said carpule; and a lock connected to said carpule and having means by which to selectively engage said needle hub at the distal end of said cylinder, said lock being moved relative to said hub from a needle retaining position at which to engage said hub and thereby prevent the relocation of said cannula from the distal end of said cylinder to a needle releasing position at which to release the engagement of said hub and thereby permit the relocation of said cannula from said distal end.

2. The syringe recited in claim 1, wherein said lock includes an opening for receiving said needle hub therethrough, said opening having areas of relatively large and small dimension, said needle hub being received through the area of relatively small dimension when said lock is in the needle retaining position, whereby said hub is engaged by said lock to prevent relocation of said needle cannula, or said needle hub being received through the area of relatively large dimension when said lock is moved to the needle releasing position, whereby said hub is released from engagement by said lock to permit relocation of said needle cannula.

3. The syringe recited in claim 2, wherein the opening in said lock for receiving said needle hub comprises a pair of holes, said areas of relatively large and small dimension corresponding to one of said holes having a diameter which is larger than the diameter of the other of said holes.

4. The syringe recited in claim 3, wherein said pair of holes overlay one another so as to have a common axis, said pair of holes providing the opening in said lock with a keyhole configuration.

5. The syringe recited in claim 1, further including:
a piston stem interconnected with said piston to control the axial movement thereof through said carpule.

6. The syringe recited in claim 5, further including means for detachably connecting said piston stem to said piston, said means for detachably connecting having a set of resilient jaws at one end thereof for releasably engaging said piston and a screw threaded rod at the opposite end for receipt in a screw threaded receptacle of said piston stem.

7. The syringe recited in claim 6, wherein said piston has a recess formed therin, the resilient jaws of said means for detachably connecting being received by and releasably retained within the recess of said piston when said recess is located within said carpule, said resilient jaws being released from said recess, whereby said means for detachably connecting is detached from said piston when said recess is located outside said carpule.

8. The syringe recited in claim 5, further including means for detachably connecting said piston stem to said piston, said means for detachably connecting comprising a head at one end thereof releasably received by and retained within a receptacle formed in said piston and a screw threaded rod at the opposite end received in a corresponding screw threaded opening of said piston stem.

9. The syringe recited in claim 8, wherein said piston has a series of slits extending radially therethrough and communicating with the receptacle of said piston, said receptacle opening up along said slits to release the head of said means for detachably connecting therefrom, whereby said means for detachably connecting is detached from said piston in response to the application of an axial pulling force to said means for detachably connecting via said piston stem to move said piston proximally through said carpule after an injection has been administered.

10. The syringe recited in claim 1, wherein said needle hub has a plug projecting therefrom and said piston has a receptacle formed therein, said piston being advanced axially through said carpule, such that the receptacle of said piston is moved into engagement with the plug of said hub for connecting said hub to said piston at the interior of said carpule.

11. The syringe recited in claim 1, further including means by which to withdraw said needle hub into said medication carpule after an injection has been administered and said lock has been moved to the needle releasing position, such that said needle cannula is retracted within and completely surrounded by said carpule.

12. The syringe recited in claim 1, wherein said needle hub is located within and movable axially through said carpule, said lock being received at one end of said carpule for controlling the movement of said hub and the relocation of said needle cannula.

13. The syringe recited in claim 12, wherein said lock is slidable laterally across said one end of said carpule between the needle retaining and needle releasing positions to control the movement of said hub and the relocation of said cannula relative to the interior of said carpule.

14. The syringe recited in claim 1, further including means to eject said carpule from the interior of said syringe cylinder.

15. The syringe recited in claim 14, wherein said means to eject includes a raised surface projecting inwardly from said cylinder into the interior thereof to engage said carpule, said cylinder having an open face located opposite said raised surface through which said carpule is ejected when a compressive force is applied to said cylinder and to said raised surface therewithin.

16. A syringe assembly including a cylinder having proximal and distal ends, said syringe assembly further including:
a carpule located at the interior of said cylinder and containing a supply of fluid;
a needle cannula communicating with the fluid supply of said carpule and extending outwardly from the distal end of said cylinder so that fluid from said carpule may be injected by way of said cannula;
a needle hub attached to said needle cannula and received at the interior of said carpule for retaining said cannula in fluid communication with said carpule;
means by which to engage said needle hub and to relocate said hub, and the needle cannula to which said hub is attached, axially and proximally through said carpule so that said cannula is retracted within and completely surrounded by said carpule; and
locking means by which to selectively engage said needle hub at the distal end of said cylinder, said locking means being moved relative to said hub from a needle retaining position at which to engage said hub and thereby prevent a proximal relocation of said hub and a retraction of said cannula to a needle releasing position at which to release the engagement of said hub and thereby permit a proximal relocation of said hub and a retraction of said cannula.

17. The syringe assembly recited in claim 16, wherein said locking means is connected to said carpule for controlling the relocation of said hub and the retraction of said cannula.

18. The syringe assembly recited in claim 16, wherein said locking means includes an opening for receiving said needle hub therethrough, said opening having areas of relatively large and small dimension, said needle hub being received through the area of relatively small dimension when said locking means is in the needle retaining position, so that said hub is engaged by said locking means to prevent a relocation of said hub, or said needle hub being received through the area of relatively large dimension when said locking means is moved to the needle releasing position, whereby said hub is released from engagement by said locking means to permit a relocation of said hub and a retraction of said cannula.

19. The syringe assembly recited in claim 16, wherein said means by which to engage and relocate said needle hub includes a piston which is moved axially and reciprocally through said carpule for expulsing the fluid therefrom, said piston having a receptacle within which to receive and engage said needle hub at the interior of said carpule, and a piston stem connected to said piston for controlling the movement of said piston through said carpule.

20. The syringe assembly recited in claim 19, further including means by which to detachably connect said piston stem to said piston, said means to detachably connect having a set of resilient jaws at one end thereof to releasably engage said piston and a screw threaded rod at the opposite end, said piston stem having an opening formed therein for receiving said screw threaded rod.

21. A syringe including a cylinder having proximal and distal ends, said cylinder receiving a supply of fluid, and a hypodermic needle cannula extending outwardly from the distal end of said cylinder and communicating with the fluid supply thereof so that fluid may be injected from said cylinder via said cannula, said syringe also including:

a carpule located at the interior of said cylinder and containing said supply of fluid, said needle cannula communicating fluidically with said carpule and the fluid therewithin, said carpule including a piston which is moved axially therethrough so that the fluid of said carpule is expulsed via said needle cannula in order to administer an injection;

a needle hub attached to said needle cannula at the distal end of said cylinder for retaining and supporting said cannula in fluid communication with said carpule, said needle hub located within and movable axially through said carpule; and a lock connected to said carpule and slidable across one end thereof, said lock having means by which to selectively engage said needle hub at the distal end of said cylinder, said lock being moved relative to said hub from a needle retaining position, at which to engage said hub and thereby prevent both the axial movement of said hub from the distal end of said cylinder and the relocation of said cannula through said carpule, to a needle releasing position, at which to release the engagement of said hub and thereby permit the axial movement of said hub and the relocation of said cannula through said carpule.

22. A syringe assembly including a cylinder having proximal and distal ends, said syringe assembly further including:

a carpule located at the interior of said cylinder and containing a supply of fluid;

a needle cannula communicating with the fluid supply of said carpule and extending outwardly from the distal end of said cylinder so that fluid from said carpule may be injected by way of said cannula;

a needle hub attached to said needle cannula and received at the interior of said carpule for retaining said cannula in fluid communication with said carpule;

means by which to engage said needle hub and to relocate said hub, and the needle cannula to which said hub is attached, axially and proximally through said carpule so that said cannula is retracted within and completely surrounded by said carpule; and locking means connected to said carpule to selectively engage said needle hub at the distal end of said cylinder to control the relocation of said hub and the retraction of said cannula, said locking means being moved relative to said hub from a needle retaining position at which to engage said hub and thereby prevent a proximal relocation of said hub and a retraction of said cannula to a needle releasing position at which to release the engagement of said hub and thereby permit a proximal relocation of said hub and a retraction of said cannula.

* * * * *